(12) United States Patent
De Groot et al.

(10) Patent No.: US 12,007,400 B2
(45) Date of Patent: Jun. 11, 2024

(54) MILKING SYSTEM WITH DETECTION SYSTEM

(71) Applicant: LELY PATENT N.V., Maassluis (NL)

(72) Inventors: Pieter Gerlof De Groot, Maassluis (NL); Abram Christiaan Knip, Maassluis (NL)

(73) Assignee: LELY PATENT N.V., Maassluis (NL)

( * ) Notice: Subject to any disclaimer, the term of this patent is extended or adjusted under 35 U.S.C. 154(b) by 557 days.

(21) Appl. No.: 17/273,989

(22) PCT Filed: Sep. 19, 2019

(86) PCT No.: PCT/NL2019/050617
§ 371 (c)(1),
(2) Date: Mar. 5, 2021

(87) PCT Pub. No.: WO2020/067879
PCT Pub. Date: Apr. 2, 2020

(65) Prior Publication Data
US 2022/0110290 A1 Apr. 14, 2022

(30) Foreign Application Priority Data
Sep. 24, 2018 (NL) ..................................... 2021690

(51) Int. Cl.
*G01N 35/00* (2006.01)
*A01J 5/00* (2006.01)
(Continued)

(52) U.S. Cl.
CPC ...... *G01N 35/00009* (2013.01); *A01J 5/0131* (2013.01); *G01N 1/18* (2013.01);
(Continued)

(58) Field of Classification Search
CPC .... G01N 33/18; G01N 33/2888; G01N 11/00; G01N 2291/02818; G01N 29/022;
(Continued)

(56) References Cited

U.S. PATENT DOCUMENTS 5,096,828 A 3/1992 Ishizaka et al.
10,989,724 B1 * 4/2021 Holmes .................. G01N 35/02
(Continued)

FOREIGN PATENT DOCUMENTS

CN 102084247 A 6/2011
CN 103353525 A 10/2013
(Continued)

OTHER PUBLICATIONS

International Search Report, issued in PCT/NL2019/050617, dated Feb. 13, 2020.
(Continued)

*Primary Examiner* — Andre J Allen
(74) *Attorney, Agent, or Firm* — Birch, Stewart, Kolasch & Birch, LLP

(57) ABSTRACT

A milking system with a milking device, a milking control, a milk line in fluid connection with the milking device, and a sampling and analysis device to take a sample of the milk from the milk line and to analyse milk from the sample are disclosed. The milking control is arranged to control the milking device on the basis of the analysis. The sampling and analysis device includes a control unit, a tape reel provided with a tape that is lengthwise provided with a series of consecutive reagent pads that provide a detectable response in the presence of a substance in the sample, a tape mover to move the tape, a dosing device to supply a part of the sample onto a reagent pad on the tape, and a camera to obtain an image of the reagent pad supplied with the droplet, and an analysis device to analyse the obtained images to
(Continued)

Figure 1:
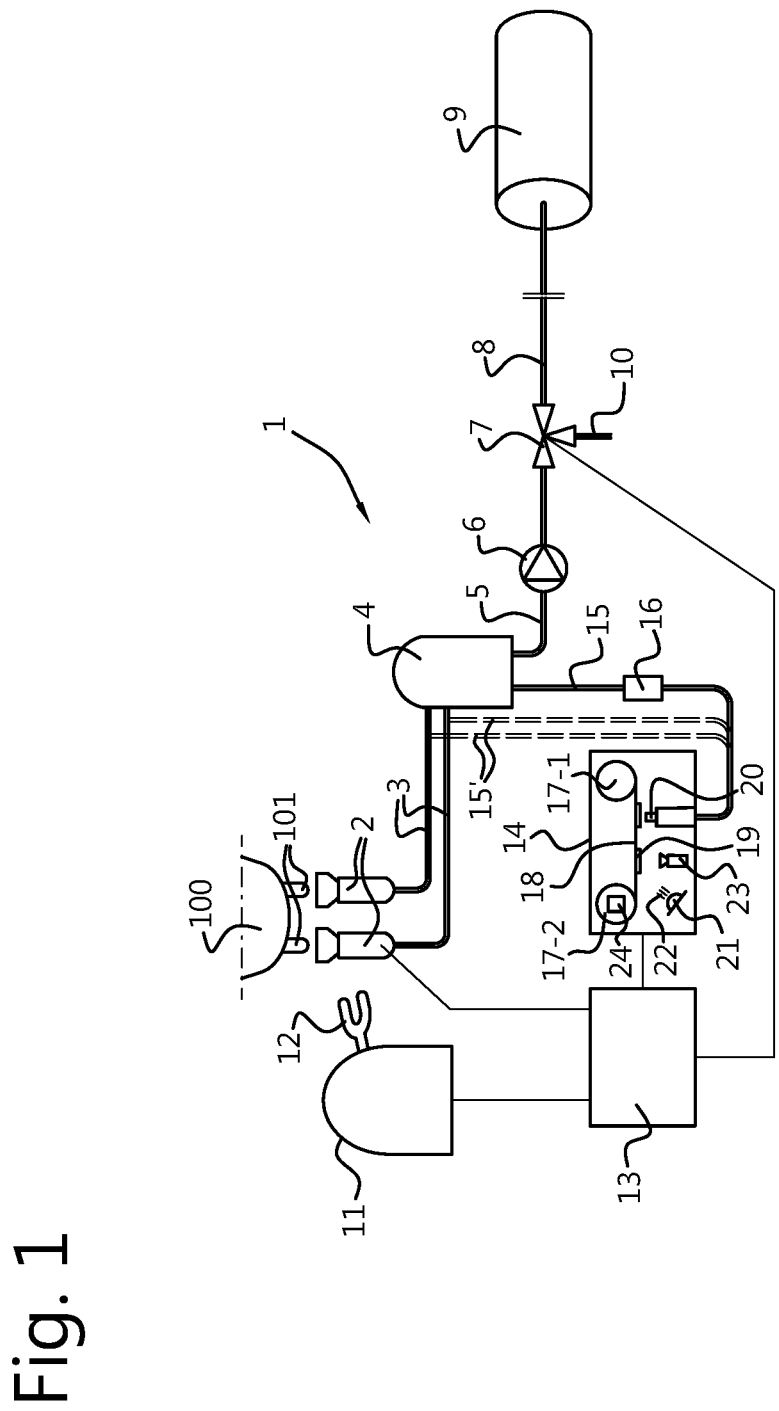

provide to the milking control device an indication of a presence or concentration of said substance. The camera has a field of view that contains a plurality of reagent pads of the series of consecutive reagent pads. This allows to observe the reaction in the reagent pad for a much longer time. In turn, this allows to use much less reagent material, such as expensive enzymes, in the pads. It is particularly useful when observing double layer reagent types.

11 Claims, 2 Drawing Sheets

(51) Int. Cl.
    *A01J 5/013*         (2006.01)
    *G01N 1/18*          (2006.01)
    *G01N 21/84*        (2006.01)
    *G01N 33/04*        (2006.01)
    *G05B 19/4155*     (2006.01)

(52) U.S. Cl.
    CPC .......... *G01N 21/8483* (2013.01); *G01N 33/04* (2013.01); *G05B 19/4155* (2013.01); *G05B 2219/45113* (2013.01)

(58) Field of Classification Search
CPC .......... G01N 29/036; G01N 2291/0256; G01N 11/16; G01N 13/02; G01N 33/1886; G01N 33/2823; G01N 33/28; G01N 13/00; G01N 11/14; G01N 2291/0423; G01N 29/222; G01N 29/024; G01N 33/4905; G01N 11/08; G01N 2291/0427; G01N 29/032; G01N 33/00; G01N 9/36; G01N 11/06; G01N 2291/0226; G01N 2001/4016; G01N 1/405; G01N 15/04; G01N 21/78; G01N 33/0031; G01N 33/2847; G01N 35/08; G01N 33/442; G01N 7/14; G01N 21/05; G01N 2291/02836; G01N 2291/02881; G01N 2291/0422; G01N 2291/0426; G01N 27/221; G01N 29/348; G01N 33/30; G01N 1/34; G01N 15/02; G01N 2001/021; G01N 2015/0092; G01N 21/8483; G01N 2291/014; G01N 2291/02416; G01N 25/18; G01N 29/46; G01N 33/0009; G01N 33/32; G01N 15/06; G01N 2013/0208; G01N 2291/0224; G01N 2291/0255; G01N 29/30; G01N 33/15; G01N 33/2858; G01N 33/44; G01N 35/1016; G01N 9/00; G01N 15/0656; G01N 2013/003; G01N 2203/0094; G01N 2291/106; G01N 29/02; G01N 33/2829; G01N 7/00; G01N 9/002; G01N 1/38; G01N 11/02; G01N 15/0205; G01N 17/00; G01N 2001/4066; G01N 2033/0091; G01N 2291/0222; G01N 25/147; G01N 29/4427; G01N 30/32; G01N 30/34; G01N 33/1826; G01N 33/2852; G01N 33/2876; G01N 33/383; G01N 11/10; G01N 2013/006; G01N 2013/0283; G01N 2021/0346; G01N 2035/00158; G01N 22/00; G01N 2291/0258; G01N 2291/02809; G01N 25/14; G01N 27/223; G01N 33/4925; G01N 35/0098; G01N 35/0099; G01N 1/12; G01N 1/4044; G01N 11/04; G01N 15/12; G01N 2015/0096; G01N 2015/1062; G01N 2035/00237; G01N 2035/00247; G01N 21/15; G01N 2291/044; G01N 25/02; G01N 27/126; G01N 27/44791; G01N 30/6095; G01N 33/0006; G01N 33/1893; G01N 33/22; G01N 33/48785; G01N 35/1095; G01N 7/10; G01N 9/24; G01N 1/10; G01N 1/14; G01N 1/2035; G01N 1/24; G01N 1/28; G01N 15/0227; G01N 19/02; G01N 2015/0038; G01N 21/03; G01N 21/0303; G01N 21/0332; G01N 21/3577; G01N 21/8507; G01N 2291/02863; G01N 27/021; G01N 27/06; G01N 27/226; G01N 3/56; G01N 30/88; G01N 33/1806; G01N 33/24; G01N 33/2835; G01N 33/287; G01N 33/4875; G01N 33/54386; G01N 35/00; G01N 35/00594; G01N 35/00693; G01N 35/00871; G01N 5/02; G01N 1/40; G01N 13/04; G01N 15/042; G01N 2013/0275; G01N 2015/0053; G01N 2015/149; G01N 2030/008; G01N 2030/025; G01N 21/648; G01N 21/85; G01N 22/04; G01N 2203/0066; G01N 2203/024; G01N 2203/0246; G01N 2291/011; G01N 2291/02433; G01N 25/08; G01N 27/026; G01N 27/127; G01N 27/286; G01N 27/403; G01N 27/4165; G01N 27/4166; G01N 27/44743; G01N 27/74; G01N 29/42; G01N 3/08; G01N 30/62; G01N 33/0073; G01N 33/03; G01N 33/146; G01N 33/1833; G01N 33/26; G01N 33/5302; G01N 33/5438; G01N 9/26; G01N 1/4077; G01N 15/1459; G01N 2011/008; G01N 2030/062; G01N 2030/326; G01N 2035/00554; G01N 2035/00752; G01N 21/293; G01N 2203/0023; G01N 2203/0092; G01N 2291/017; G01N 2291/0215; G01N 2291/101; G01N 3/00; G01N 30/16; G01N 31/22; G01N 33/0011; G01N 33/487; G01N 33/54373; G01N 35/00712; G01N 1/22; G01N 1/2214; G01N 1/2247; G01N 1/2273; G01N 15/0266; G01N 15/05; G01N 15/065; G01N 17/002; G01N 19/10; G01N 2009/006; G01N 2013/0225; G01N 2013/0241; G01N 2015/0288; G01N 2015/045; G01N 2015/0687; G01N 2015/1075; G01N 2015/1087; G01N 2015/1486; G01N 2021/054; G01N 2021/152; G01N 2021/3595; G01N 2021/6439; G01N 2030/128; G01N 2030/204; G01N 2030/324; G01N 2030/342; G01N 2035/00683; G01N 2035/1032; G01N 2035/1062; G01N 21/33; G01N 21/53; G01N 21/64; G01N 21/6428; G01N 21/6486; G01N 21/65; G01N 21/7703; G01N 21/91; G01N 2203/0085; G01N 2203/027; G01N 2223/076; G01N 2291/02845; G01N 2291/02872; G01N 2291/0421; G01N 2291/102; G01N 23/223; G01N 27/04; G01N 27/128; G01N 27/18; G01N 27/307; G01N 27/3272; G01N 27/3273; G01N 27/3275; G01N 27/38; G01N 27/4145; G01N 27/416; G01N 27/4163; G01N 27/447; G01N 27/60; G01N 27/745; G01N 29/14; G01N 29/2462; G01N 29/2481; G01N 29/343; G01N 29/4436; G01N 29/4481; G01N 3/02; G01N 3/40; G01N 30/00; G01N 30/02; G01N 30/12; G01N 30/20; G01N 30/463; G01N 30/8675; G01N 31/222; G01N 33/0016; G01N 33/0034; G01N 33/02; G01N 33/14; G01N 33/205; G01N 33/241; G01N 33/2805; G01N 33/2811; G01N 33/2817; G01N 33/48707; G01N 33/48757; G01N 33/49; G01N 33/4915; G01N 33/493; G01N 33/497; G01N 33/528; G01N 33/80; G01N 33/84; G01N 33/92; G01N 35/028; G01N 35/085; G01N 35/10; G01N 5/00; G01N 9/04; G01N 9/32; G01N 1/16; G01N 1/2202; G01N 1/2208; G01N 15/082; G01N 15/1456; G01N 17/008; G01N 2001/2057; G01N 2001/2064; G01N 2001/2223; G01N 2001/2267; G01N 2001/4027; G01N 2001/4088; G01N 2011/0046; G01N 2011/006; G01N 2011/0066; G01N 2015/0073; G01N 2015/0675; G01N 2015/0693; G01N 2015/105; G01N 2015/1093; G01N 2021/0325; G01N 2021/0382; G01N 2030/065; G01N 2035/00217; G01N 2035/00524; G01N 2035/00534; G01N 2035/1018; G01N 2035/1044; G01N 21/3504; G01N 21/359; G01N 21/82; G01N 2203/0284; G01N 2203/0286; G01N 2203/0623; G01N 2203/0682; G01N 2291/0253; G01N 2291/0254; G01N 27/00; G01N 27/02; G01N 27/07; G01N 27/10; G01N 27/121; G01N 27/122; G01N 27/22; G01N 27/3271; G01N 27/36; G01N 2800/52; G01N 29/11; G01N 3/32; G01N 30/0005; G01N 30/06; G01N 30/64; G01N 30/7206; G01N 30/8658; G01N 31/00; G01N 33/0047; G01N 33/1846; G01N 33/5005; G01N 33/54306; G01N 33/54393; G01N 33/558; G01N 35/026; G01N 35/04; G01N 35/1097; G01N 37/005; G01N 9/12; G01N 1/00; G01N 1/04; G01N 1/2042; G01N 1/2205; G01N 1/26; G01N 1/30; G01N 1/312; G01N 1/36; G01N 1/4005; G01N 1/4022; G01N 1/44; G01N 11/167; G01N 15/00; G01N 15/0272; G01N 15/0625; G01N 15/0631; G01N 15/0826; G01N 15/088; G01N 15/0893; G01N 15/1031; G01N 15/1218; G01N 15/14; G01N 15/1404; G01N 15/1434; G01N 15/147; G01N 15/1484; G01N 17/006; G01N 17/046; G01N 2001/022; G01N 2001/1093; G01N 2001/1427; G01N 2001/2217; G01N 2001/2232; G01N 2001/2282; G01N 2001/4011; G01N 2011/004; G01N 2011/0073; G01N 2011/0093; G01N 2013/025; G01N 2015/0011; G01N 2015/0065; G01N 2015/008; G01N 2015/0233; G01N 2015/035; G01N 2015/0668; G01N 2015/084; G01N 2015/0866; G01N 2015/1006; G01N 2015/1025; G01N 2015/1081; G01N 2015/144; G01N 2015/145; G01N 2015/1493; G01N 2021/258; G01N 2021/6478; G01N 2021/6482; G01N 2021/6484; G01N 2021/772; G01N 2021/8477; G01N 2030/009; G01N 2030/121; G01N 2030/146; G01N 2030/201; G01N 2030/207; G01N 2030/3007; G01N 2030/328; G01N 2030/347; G01N 2030/521; G01N 2030/565; G01N 2030/625; G01N 2030/645; G01N 2030/746; G01N 2030/765; G01N 2030/8447; G01N 2030/8804; G01N 2030/8809; G01N 2030/8813; G01N 2030/8831; G01N 2030/885; G01N 2030/8854; G01N 2030/8881; G01N 2033/0095; G01N 2035/00089; G01N 2035/00198; G01N 2035/00326; G01N 2035/00574; G01N 2035/0425; G01N 2035/1034; G01N 2035/1046; G01N 21/23; G01N 21/29; G01N 21/3103; G01N 21/4133; G01N 21/532; G01N 21/552; G01N 21/554; G01N 21/643; G01N 21/6445; G01N 21/645; G01N 21/6454; G01N 21/6458; G01N 21/68; G01N 21/76; G01N 21/7743; G01N 21/79; G01N 21/81; G01N 21/84; G01N 21/93; G01N 21/94; G01N 2201/0218; G01N 2201/0227; G01N 2201/024; G01N 2201/061; G01N 2203/0025; G01N 2203/0226; G01N 2203/0232; G01N 2203/0256; G01N 2203/0296; G01N 2203/0676; G01N 2203/0688; G01N 2291/02408; G01N 2291/02466; G01N 2291/056; G01N 23/125; G01N 23/20; G01N 23/203; G01N 2333/575; G01N 2333/62; G01N 2333/75; G01N 2333/90209; G01N 2446/00; G01N 2458/00; G01N 25/00; G01N 25/085; G01N 25/12; G01N 25/48; G01N 25/52; G01N 25/66; G01N 2570/00; G01N 2600/00; G01N 27/023; G01N 27/025; G01N 27/125; G01N 27/27; G01N 27/28; G01N 27/30; G01N 27/302; G01N 27/305; G01N 27/327; G01N 27/3276; G01N 27/401; G01N 27/414; G01N 27/4143; G01N 27/4162; G01N 27/4167; G01N 27/423; G01N 27/44726; G01N 27/44752; G01N 27/44756; G01N 27/62; G01N 27/70; G01N 27/72; G01N 2800/042; G01N 2800/122; G01N 2800/28; G01N 2800/32; G01N 29/2412; G01N 29/345; G01N 29/38; G01N 3/12; G01N 3/18; G01N 3/20; G01N 3/24; G01N 30/10; G01N 30/24; G01N 30/36; G01N 30/466; G01N 30/52; G01N 30/56; G01N 30/6026; G01N 30/6034; G01N 30/6086; G01N 30/6091; G01N 30/66; G01N 30/72; G01N 30/7233; G01N 30/74; G01N 30/76; G01N 30/84; G01N 30/8651; G01N 30/8665; G01N 30/8679; G01N 30/96; G01N 31/16; G01N 31/221; G01N 33/0001; G01N 33/0004; G01N 33/0013; G01N 33/0014; G01N 33/0037; G01N 33/004; G01N 33/0044; G01N 33/0049; G01N 33/025; G01N 33/04; G01N 33/08; G01N 33/1813; G01N 33/182; G01N 33/186; G01N 33/1866; G01N 33/188; G01N 33/225; G01N 33/246; G01N 33/2841; G01N 33/34; G01N 33/343; G01N 33/36; G01N 33/42; G01N 33/48; G01N 33/483; G01N 33/48714; G01N 33/48771; G01N 33/491; G01N 33/492; G01N 33/50; G01N 33/5029; G01N 33/5091; G01N 33/5097; G01N 33/52; G01N 33/521; G01N 33/5308; G01N 33/54326; G01N 33/54388; G01N 33/56938; G01N 33/582; G01N 33/66; G01N 33/6812; G01N 33/6839; G01N 33/6842; G01N 33/6854; G01N 33/6872; G01N 33/6893; G01N 33/6896; G01N 33/74; G01N 33/743; G01N 33/86; G01N 33/94; G01N 35/00029; G01N 35/00069; G01N 35/02; G01N 35/021; G01N 35/025; G01N 35/1002; G01N 35/1011; G01N 35/1074; G01N 9/08; G01N 9/14; G01N 9/18; G01N 9/28; G01N 1/08; G01N 1/2294; G01N 11/12; G01N 11/162; G01N 15/0606; G01N 15/0618; G01N 15/10; G01N 19/04; G01N 2001/2276; G01N 2015/0046; G01N 2015/1254; G01N 2021/8528; G01N 2021/8557; G01N 2030/027; G01N 2030/3084; G01N 2035/00188; G01N 2035/00495; G01N 2035/00881; G01N 2035/0403; G01N 2035/0406; G01N 2035/0412; G01N 2035/0441; G01N 2035/1006; G01N 2035/1025; G01N 21/1702; G01N 21/251; G01N 21/253; G01N 21/272; G01N 21/274; G01N 21/31; G01N 21/37; G01N 21/59; G01N 21/77; G01N 2201/128; G01N 2291/012; G01N 2291/0217; G01N 2291/0257; G01N 2291/103; G01N 2291/2698; G01N 27/26; G01N 27/4175; G01N 27/44704; G01N 27/622; G01N 2800/54; G01N 29/041; G01N 29/223; G01N 29/228; G01N 29/4472; G01N 30/28; G01N 30/30; G01N 30/54; G01N 30/86; G01N 33/0022; G01N 33/0026; G01N 33/0032; G01N 33/0075; G01N 33/1853; G01N 33/20; G01N 33/208; G01N 33/2894; G01N 33/53; G01N 33/5306; G01N 33/54353; G01N 33/54366; G01N 33/5748; G01N 35/00732; G01N 35/1009; G01N 37/00; G01N 5/04; A01J 5/01; A01J 5/0134; G05D 11/139; G05D 11/132; G05D 11/135; G05D 21/02; G05D 23/1919; G05D 7/0647; G05D 7/0694; G05D 9/12

USPC .......................................... 73/53.01

See application file for complete search history.

(56) References Cited

U.S. PATENT DOCUMENTS

| | | |
|---|---|---|
| 11,112,418 B1* | 9/2021 | Holmes ................. G01N 35/04 |
| 11,360,107 B1* | 6/2022 | Young ................... G01N 35/1016 |
| 2009/0255473 A1 | 10/2009 | Katz et al. |
| 2015/0122183 A1 | 5/2015 | Oggier |
| 2017/0099801 A1 | 4/2017 | Van Tilburg et al. |
| 2021/0185972 A1* | 6/2021 | Gavin ..................... A01J 5/007 |
| 2021/0195863 A1* | 7/2021 | Gavin ..................... G01N 1/10 |
| 2021/0315181 A1* | 10/2021 | Knip ..................... G01N 1/2035 |
| 2021/0329877 A1* | 10/2021 | Dessing ............. G01N 15/0612 |
| 2021/0341447 A1* | 11/2021 | Gavin ..................... G01N 33/04 |

FOREIGN PATENT DOCUMENTS

| | | |
|---|---|---|
| CN | 103439504 A | 12/2013 |
| CN | 105784722 A | 7/2016 |
| CN | 105806816 A | 7/2016 |
| CN | 106282312 A | 1/2017 |
| CN | 106455517 A | 2/2017 |
| CN | 207096261 U | 3/2018 |
| EP | 1 537 775 A1 | 6/2005 |
| WO | WO02/069697 A1 | 9/2002 |
| WO | WO2004/034063 A2 | 4/2004 |
| WO | WO2004/034063 A3 | 4/2004 |
| WO | WO2012/134379 A1 | 10/2012 |

OTHER PUBLICATIONS

Written Opinion of the International Searching Authority, issued in PCT/NL2019/050617, dated Feb. 13, 2020.

* cited by examiner

MILKING SYSTEM WITH DETECTION SYSTEM

The present invention relates to a milking system, comprising a milking means with a milking control device and arranged for milking milk from a dairy animal, a milk line in fluid connection with the milking device, a sampling and analysis device arranged to take a sample of the milk from the milk line and to analyse milk from the sample, wherein the milking control device is arranged to control the milking means on the basis of the analysis of the milk sample, wherein the sampling and analysis device comprises a control unit for controlling the sampling and analysis device, a tape reel provided with a tape that is lengthwise provided with a series of consecutive reagent pads that are configured to provide a detectable response in the presence of at least one substance in the sample, a tape mover, arranged to move the tape under control of the control device, a dosing device arranged to supply a part of the sample onto a reagent pad on the tape under the control of the control unit, a camera device operably connected to the control unit, and arranged to obtain an image of said reagent pad supplied with said droplet of the sample, and an analysis device to analyse the obtained images to provide to the milking control device an indication of a presence or concentration of said at least one substance.

Such milking systems are in principle known, and they are arranged to analyse milk on the basis of one or more camera images of the reagent.

In practice, it turns out that the known systems are not always satisfactory with regard to the use of reagent and/or the throughput of milking the dairy animals.

Therefore, it is an object of the present invention to provide a milking system of the kind mentioned above, that pairs a high throughput with a relatively low use of reagents.

The above object is at least partially achieved by means of a milking system according to claim 1, in particular a milking system comprising a milking means with a milking control device and arranged for milking milk from a dairy animal, a milk line in fluid connection with the milking device, a sampling and analysis device arranged to take a sample of the milk from the milk line and to analyse milk from the sample, wherein the milking control device is arranged to control the milking means on the basis of the analysis of the milk sample, wherein the sampling and analysis device comprises a control unit for controlling the sampling and analysis device, a tape reel provided with a tape that is lengthwise provided with a series of consecutive reagent pads that are configured to provide a detectable response in the presence of at least one substance in the sample, a tape mover, arranged to move the tape under control of the control device, a dosing device arranged to supply a part of the sample onto a reagent pad on the tape under the control of the control unit, a camera device operably connected to the control unit, and arranged to obtain an image of said reagent pad supplied with said droplet of the sample, and an analysis device to analyse the obtained images to provide to the milking control device an indication of a presence or concentration of said at least one substance, wherein the camera device has a field of view that contains a plurality of reagent pads of the series of consecutive reagent pads.

A milking system requires a relatively high throughput, as determined by the time period between consecutive milkings. In practice, this time period varies, but may be as short as a few minutes, for example when a cow is milked just after milking a cow with a small production or at least a short milking time. If the sampling and analysis device would have to sample and analyse the milk of the dairy animal in the same rhythm this would thus lead to a relatively short time for the (chemical or other) reaction in the reagent pad. In turn, this requires a high amount or concentration of the reagent(s) in the reagent pad. Many of these reagents are enzymes or other biological products that are quite difficult to make, and thus require quite some resources. Alternatively, when using less reagent in the pad, it takes longer before a reliable analysis can be performed, which in turn would lower the throughput through the milking system.

The inventors have realised that it is possible to make more time available for the reaction, and thus the analysis, by allowing the camera device to observe the reagent pad for longer than one sampling period. This is achieved by keeping a reagent pad in the field of view even when the reagent tape is shifted one or more positions to a further reagent pad. In other words, the field of view of the camera should be arranged such that the reagent pad is in view for more than one sampling period. This allows the available reaction time to at least double, thereby allowing the use of a much lower reagent concentration. In this respect, it is stressed that "ha[ving] a field of view that contains a plurality of reagent pads of the series of consecutive reagent pads" relates to reagent pads in a consecutive series, that are displaced stepwise, and will shift into the field of view, remain there for at least two different positions, and will then be shifted out of the field of view again. It does not relate to two or more reagent pads that might be arranged side-by-side in sets, the sets each being shifted into or out of the field of view at the same time. It is of course still possible to have such an arrangement, but it would then require that two or more consecutive sets of reagent pads be present in the field of view.

Herein, it is furthermore noted that the pads should be in the field of view completely, in order to allow a good analysis of the image thereof. It is furthermore noted that controlling the milking on the basis of the analysis of the milk sample could be in-line, i.e. for the current milking, or "off-line", i.e. for a subsequent milking. This depends for example on the type of sample. A sample taken from the foremilk leaves some time for sampling and analysing, in most cases a number of minutes. Contrarily, a sample taken from the main milk often requires subsampling during all of the milking in order for the sample to be representative for the milk. This means that the analysis can only take place after the milking proper, which would almost inevitably lead to a lower throughput. Thus, in most cases the milking control unit will control the milking based on an analysis result from one or more previous milkings. Thereto, the analysis device can provide the milking control unit with an analysis result signal, or at least a signal for the milking control unit to be processed. Such a signal could be an attention signal, for example if the concentration of the particular substance(s) is (are) higher than a threshold value, or sometimes lower than a threshold value, such as in the case of progesterone, where a too low value indicates (near) heat. It is remarked that "substance" may include entities such as "somatic cells".

Particular embodiments and advantages are described in the appended dependent claims, as well as in the now following part of the description.

In embodiments, the tape mover is arranged to move the tape from a first position to a second position, wherein the sampling and analysis device is arranged to obtain images in at least the first position and the second position and to analyse said images obtained in at least the first position and the second position in order to provide said indication of a presence or concentration of said at least one substance. This allows to make use of the fact that, according to the invention, a reagent pad can be in view of the camera in more than one position. In use of the reagent tape, the tape will move forward one pad length per sampling. Advantageously, therefore, the second position is shifted with respect to the first position over a predetermined distance, in particular the effective length of one reagent pad of the series of consecutive reagent pads, such that a next reagent pad comes into the field of view of the camera device. Herein, "effective length" relates to a centre-to-centre distance between consecutive pads. The sampling and analysis device is arranged for supplying said part of the sample onto a reagent pad of the series of consecutive reagent pads. This is done at some time before obtaining the images with the response, and it may be performed in situ, i.e. at the position where the images are obtained. More often, obtaining the images is performed in a different position. For example, the sample is supplied to a reagent pad at a starting or sampling position. The reagent pad is then shifted to the first position, this position being in the field of view of the camera device. When a subsequent sample is taken, such as for a subsequent milking, the reagent pad is shifted to the second position, and so on. Some time in the meantime, the camera device obtains at least one image. This image may be taken while the reagent pad is in the first position, or when it is already in the second position, or even further down. This depends on the criterion for obtaining an image. Sometimes a single image suffices, when taken after a certain time period has passed, such as 10 minutes. If this period is shorter than the time for milking the subsequent animal, the reagent pad will have been shifted into the second position before the image is obtained. However, in many cases the measurement accuracy and precision improves when a number of images is obtained and processed. In that case at least a first image will have been obtained in the first position. One or more subsequent images will then be obtained in either the first position, the second position, or even a further position still within the field of view. This depends on whether or not the tape with the reagent pads needs to be shifted to accommodate a sampling of a subsequent dairy animal. After all, that not only depends on the time duration of a milking, but also on the lapsed time until a new animal presents itself to be milked and sampled. If there is a row of animals waiting to be milked, and all are allowed to be milked for consumption milk, then a subsequent sampling will take place right after a previous milking/sampling. But it is possible that quite some time will have lapsed until a next milking/sampling, such as during the night, when milking is less frequent, or if there are one or more animals that are not allowed to be milked, because they produce unfit milk due to illness or have been milked too recently. Again, from all this it follows that in particular in voluntary robotic milking systems the present invention provides advantages, in that it is more flexible as to the time(s) when a subsequent sample may be taken and when images of a previous sample may be obtained, and then processed.

In embodiments, the camera device is arranged such as to have said field of view contain two, three or four reagent pads of the series of consecutive reagent pads. Having two reagent pads in the field of view of the camera device already provides a lot of extra time for obtaining images and then analysing same. Still, having three or four reagent pads in the field of view stretch these possibilities even further, while still ensuring that the camera device collects sufficient information for the analysis. After all, optical camera devices have a very high resolution these days, while even infrared or other camera devices will still have a sufficient resolution when two or more, such as up to four images in a row are in the field of view of the camera. Of course, other, higher numbers are possible, all depending on the required resolution and the properties of the available camera device.

Herein, it is noted that the field of view depends on the optical properties of the camera, notably its lens system. If the field of view is to have a certain size, then either the lens system for the camera device is selected accordingly, such as a wide angle lens, or the object distance is increased, or a combination thereof. This, however, is a simple exercise for the skilled person.

In embodiments, the analysis device is arranged to obtain images of one of said reagent pads during at least a predetermined period of time, said predetermined period of time being at least as long as a multiple of an average length of time of milking one of said dairy animals. This ensures in most cases, save the ones in which milking is done with difficulty or with a slowmilking animal or the like, that there is sufficient time to obtain images during two milkings, i.e. longer than in known systems. In particular, said predetermined period of time amounts to at least 10 minutes, more preferably at least 15 minutes, yet more preferably at least 20 minutes. Based on the selected period of time, the corresponding number of reagent pads in the field of view and the properties of the camera device may be attuned. In turn, the reagent(s) and/or their concentration(s) may be selected to achieve a sufficient measurement precision within such timeframe. again, this is a straightforward exercise for the skilled person, and could easily be done by way of some experiments.

In embodiments, the sampling and analysis device is arranged to simultaneously analyse the respectively milked milk of a plurality of consecutively milked dairy animals. Although it follows in principle as a possibility that is based on the features and advantages described above, it is pointed out here that two or more samples may be followed and analysed simultaneously. For example, a first reagent pad with a first sample is already in the second position mentioned above, while a subsequent second reagent pad with a second sample is in the first position. The camera device that obtains images will then have two reagent pads, each with a sample, in its field of view. In this case both reagent pads are in the process of being imaged and analysed, which is possible according to the invention. the analysis device can do this because it can analyse a part of the image that corresponds to the first reagent pad and sample separately from another part of the image that corresponds to the second reagent pad and sample. The analysis device is in such case arranged to process the images accordingly, i.e. follow a reagent pad in the images, in order to collect relevant information about one and the same reagent pad in different images in which that reagent pad has shifted position.

Of course, it could be that a lot of time has passed since the first sample was analysed. In such a case it is possible that during the time allotted for the analysis the first reagent pad did not shift at all, which makes the analysis for that situation all the more simple. Furthermore, in accordance with embodiments pointed out above, the sampling and analysis device is arranged to simultaneously analyse the respectively milked milk of preferably between two and four dairy animals. This allows ample time for an analysis. Yet, other numbers are not excluded.

In advantageous embodiments, the reagent pad comprises a bottom layer near the tape and stacked thereon a top layer, wherein at least the bottom layer comprises a reagent material configured to provide a detectable response in the presence of at least one substance in the sample, and wherein the top layer causes a first reaction before said detectable response can occur. Such double layers may prove advantageous for various reasons and/or in various circumstances. First, it is possible to have the top layer protect the bottom layer against influences, such as of oxygen, moisture or the like, as long as the top layer is penetratable by the sample liquid, such as dissolvable or the like. This allows much more accurate measurements in the case of particularly sensitive reagent materials. Second, the response may require a two-step reaction with per se incompatible reagent materials, such as a specific acid and a specific base, or the reaction product of the first reaction, in the top layer, is required for another reaction, in the bottom layer, and so on. In such cases, it is desirable to have more time available for observing the response, which is what is provided by the present invention.

Figure 2:
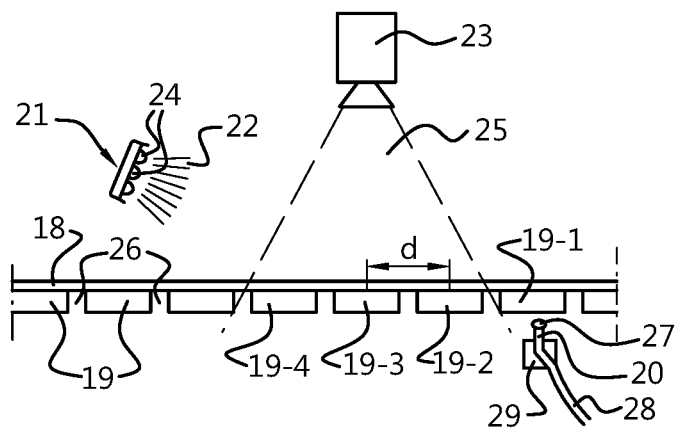
Figure 3:
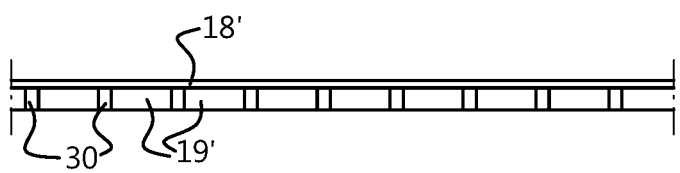
Figure 4:
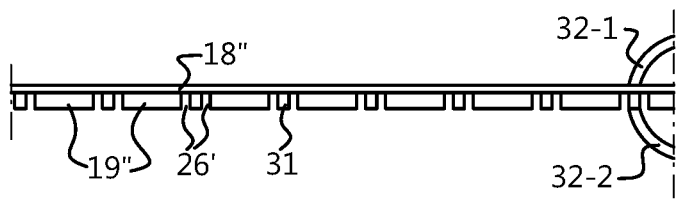

The invention will now be elucidated by way of a number of exemplary embodiments and the drawings, in which FIG. 1 shows a diagrammatic representation of a milking system according to the present invention;

FIG. 2 diagrammatically shows a detail of a milking system according to the invention; and FIGS. 3 and 4 diagrammatically show a yet smaller detail of other embodiments of the invention.

FIG. 1 shows a diagrammatic representation of a milking system 1 according to the present invention for milking teats 101 of an udder 100 of a dairy animal. The milking system 1 comprises teat cups 2, connected to short milk lines 3, debouching in a milk jar 4, that in turn is connected to a main milk line 5. A milk pump is denoted 6, and a three-way valve with 7 connects to a bulk tank line 8 connected to a bulk milk tank 9, and to a sewer line 10.

A milking robot 11 has a robot arm 12 and a robot control unit 13. A sampling unit is generally denoted 14, and a sampling line 15 with an optional sample valve 16. the sampling unit 14 comprises a supply reel 17-1 and a collecting reel 17-2 for a tape 18 with reagent pads 19. A nozzle device for sample droplets is denoted by 20, a light source 21 emits light 22, a camera is denoted by 23, and a tape mover by 24.

In use of the milking system 1, the robot control unit 13 controls the milking robot 11 with the robot arm 12 to attach the teat cups 2 to the teats 101 of the udder 100 of a dairy animal such as a cow. The milk that is subsequently milked leaves the teat cups 2 under the influence of a vacuum, that is applied by a pump not depicted here, via the short milk lines 3, and is collected in a milk jar 4.

In order to comply with legal requirements, the first milk from each teat must be tested for physical changes, and if desired for other deviant properties. This can be done by means of a separate foremilk test device, or it can be done with the help of the sampling unit 14 as supplied according to the invention. Then use will be made of the alternative sample lines 15'. In case of a negative assessment, the milked milk collected in the milk jar 4 will then be pumped to the sewer line 10 by means of the milk pump 6, via the main milk line 5 and the three way valve 7. All these devices are under the control of the robot control unit 13. Contrarily, if the milk is assessed to be OK, it will be pumped to the bulk milk tank 9 via the bulk line 8.

It is also possible that the sampling unit 14 takes a sample from the milk jar 4, in particular a mixed sample from milk that was milked from all teats and during all of the milking. This helps to get a good assessment of the milk that (if not rejected based on the foremilk assessment or otherwise, such as being antibiotics milk) will be sent to the bulk tank 9, or possible to one of several bulk milk tanks. For example, the milk from different cows could be sent to different bulk tanks, based on their fat content, their protein content or otherwise, as determined by the sampling unit 14. In such embodiments, as the one shown in FIG. 1, the sample line 15 runs from the milk jar 4 to the sampling unit 14, and optionally has a sample valve 16. Note that the latter could also be a part internal to the sampling unit 14.

Most often, however, the sampling unit 14 is used to determine a property of the milk from a cow, either per teat quarter 101 or for the whole udder 100/animal, which property is subsequently used in animal management but not for immediate control of the milk destiny. Examples are the measurement of hormones such as progesterone, that play a role in the reproductive cycle of the animal, or of substances that relate to feeding or metabolic health of the animal. Based on the assessment by the sampling unit 14, the farmer or the control unit 13 may then adapt feeding, call a veterinary for a health check or for insemination, and so on.

Furthermore, a sampling unit 14 is very generally shown, in that it here contains a supply reel 17-1 and a collecting reel 17-2, between which a tape 18 is wound down by means of the tape mover 24, such as a cassette deck motor or stepper motor. The tape 18 carries reagent pads 19 that contain reagent that gives a detectable response in the presence of a defined substance, often the intensity of the response depending on the concentration of the substance brought into the reagent via the sample droplet. Such a sample droplet is delivered via the nozzle 20. A light source 21 then shines light 22 onto the reagent pad 19, and a camera 23 observes the response, if any, in the reagent pad. The light source 21 may be any suitable light source, such as one or more LEDs, and the emitted light 22 may be visible light, UV(A) radiation, (near) infrared, and so on, depending on the used reagent. Of course, the camera 23 should be adapted to detect radiation coming from the reagent pad 19. Often, this is reflected or scattered light, but it could be different radiation, such as fluorescence radiation. In any case, details of such radiation and detection may easily be implemented by the skilled person and do not form the present invention as such.

It is remarked here that the camera 23 and the light source 21 are shown below the tape 18 with the reagent pads 19. In practice, it may also occur, and in fact often be advantageous, if the camera 23 and the light source 21 are positioned above the tape 18. This allows the camera to image the reagent pad to which the sample droplet is supplied without advancing the tape, i.e. immediately. In addition, there is no risk of any liquid, or dirt, falling from the reagent pad to the camera and/or light source. Moreover, in general, it is advantageous if the camera 23 and/or the light source 21 are positioned outside the sampling unit 14, or rather outside a housing of the sampling unit. The camera and the light source are still functional parts of the sampling unit as a whole, but the former two parts are positioned outside a housing with the tape (reels) and the supply nozzle 20.

FIG. 2 diagrammatically shows a detail of a milking system according to the invention. Herein, similar parts are denoted by the same reference numerals. The present embodiment shows a tape 18 with first through fourth reagent pads 19-1 through 19-4. A light source 21 has three LEDs and emits light 22. The camera 23 has a field-of-view 25. Between two neighbouring reagent pads there is a laser ablation line 26. The nozzle doses a droplet 27 of a milk sample delivered by a sample supply line 28 to the first reagent pad 19-1. Finally, an overflow cup to catch excessive fluid ejected by the nozzle is denoted by 29.

In this embodiment, the camera 23 is mounted above the tape 18, with the reagent pads 19-1 through 4 facing down, i.e. away from the camera 23. This is advantageous in that the camera can now see the reaction in the pads without being hindered by colour already developed, or by remnants of the droplet 27 of milk sample, in case that would not yet have been fully absorbed by the respective pad. Of course, the tape 18 should be sufficiently transmissive for the radiation 22, but that does not pose any specific problems to the skilled person. Such tape 18 could e.g. be a polyester-like material. Another advantage is that any surplus sample liquid, or dust or other dirt does not fall onto or even into the camera 23 or light source 21. Note that it is actually the optical path that counts, for it is possible to position a mirror above the tape 18 and under a 45 degree angle, and have the camera 23 look into the mirror horizontally. Thus, it is not the physical position that counts, but the position of the camera as seen by the tape 18 and pads 19 ( . . . ). Such mirror set-up may be advantageous if space is at a premium, for it is more compact.

In the embodiment shown, the nozzle 20 receives milk, or some other liquid sample, from the sample supply line 28, as dosed by a non-shown dosing or metering means. Hereby, a droplet 27 is formed, that is applied to the reagent pad 19-1. At the same time, there are three other reagent pads, viz. 19-2, 19-3 and 19-4, still in the field-of-view 25 of the camera 23. These three reagent pads had been supplied with a sample droplet one, two, three samplings/milkings ago, respectively. The camera 23 was able to follow the development of the reaction in these reagent pads during the past one, two, or three milkings, although it is noted that sampling need not take place during each milking. This being able to follow the development of the response in the pad has a big advantage, in that the concentration of the reagent (enzyme or the like) need not be as high as would be required for a quick response, i.e. one that gives similar results/intensities but then during the time period of one milking. Such time is on average about 8 to 10 minutes, but may be as short as 5 or 6 minutes. By now being able to observe the response during a time that is four times longer, it can be increased to about 20 to 40 minutes. This allows a much more efficient use of the reagents, which are often hard to produce.

In the present embodiment, there are four reagent pads 19-1 through 4 in the field-of-view 25 of the camera 23. This is still OK, because the resolution of optical camera such as ccd cameras is sufficient in most cases. However, in case the speed of the response is sufficiently high, it may suffice to have a smaller number of reagent pads 19 in the field-of-view of the camera, such as 2 or three reagent pads. this allows a larger apparent size of the reagent pad in the camera's image, and thus a more precise assessment of that image.

In use, the droplet 27 has been provided to the reagent pad 19-1. Just before sampling a subsequent animal, the tape 18 will be shifted to a new and unused reagent pad over one reagent pad length, i.e. over a distance d in the FIG. 2, the centre-to-centre distance between two consecutive reagent pads. This may be done under the control of the camera, and its image processing/control unit, cfr. control unit 13 of FIG. 1. Thereto, the camera takes an image of the tape 18 with at least one reagent pad, here three reagent pads 19-1 . . . 3, and with the laser ablation lines 26 between each reagent pad and its neighbours. Such ablation line 26 is visible as the absence of the reagent material, i.e. mostly as a dark line in the image. In addition, laser ablation will leave a thin more or less charred surface of the reagent material. Furthermore, although the Figure shows a relatively wide ablation line 26, in practice this can be made very narrow, e.g. as narrow as about 0.1 mm. This allows a very precise positioning of the ablation lines and thus of the reagent pads.

When the system is to move the tape 18 to the next position, i.e. a shift over one centre-to-centre distance d, the tape mover (not shown here, but 24 in FIG. 1) is controlled to move the tape 18 until the position of the ablation line taken as the starting point is assumed by the very next ablation line. In the presently shown embodiment, this can be done for more than one ablation line 26, here up to five ablation lines, so that through error correction the displacement is even more reliable and accurate.

It is noted that it is possible to shift the tape 18 over more than one centre-to-centre distance d. For example, in case of doubt as to the quality of the very next reagent pad, it is possible to move the tape 18 over, say, two or more times the distance d. This may be compared with advancing a roll of film in an analogue camera, after loading it into the camera. The first few exposures would have been bad because of light reaching the film, and so they are advanced anyway. A similar reason in the present embodiment could be that there is a high temporary moisture load, e.g. due to exchange of a reel of tape, or maintenance or the like, so that the first few new reagent pads have a substandard quality. It is then safer to forward those few reagent pads in one go, and thereto the tape 18 is advanced over a few timed the distance d.

FIGS. 3 and 4 diagrammatically show a yet smaller detail of other embodiments of the invention. FIG. 3 shows a tape 18' with reagent pads 19' that are separated by thin layers or zones 30 of added hydrophobic barrier material. In this embodiment, no reagent material is removed from the continuous layer, but rather, separate reagent pads 19' have been created by adding a hydrophobic barrier material in a narrow zone 30 into the reagent material. thereto, a suitable material, such as a TFE polymer, paraffin or the like. This is pressed onto and into, or injected into, a continuous layer of reagent material such that hydrophobic barrier lines 30 are formed between (now) separated reagent pads 19'. These lines 30 may be formed by means of per se well-known printing techniques or the like. These zones 30 may be made narrow as well, but are often less well-controlled as to their width, due to the requirement that the hydrophobic material is absorbed the reagent material. This is advantageous to prevent the sample liquid from traveling to a neigbouring pad near the tape 18, i.e. at the bottom of the pads. Note also that, because the camera 23 looks through the tape, it is the bottom of the zone 30, near the tape 18', that will be used for positioning. In this respect, laser ablation lines are advantageous, since controlling these to reach the bottom of the reagent material, i.e. reaching the tape 18', is more easily possible. Still, forming such zones 30 by means of injecting a hydrophobic barrier material is well possible, and may also be used to position the tape 18' with the reagent pads 19'. In this case, having more pads in view of the camera adds accuracy, in that an averaged thickness of the zones 30 as determined in the total image will be used for positioning.

FIG. 4 shows a detail of yet another embodiment, in which the reagent pads 18" are separated by a set of two laser ablation lines 26', with a narrow remaining zone 31 remaining between the two lines. Parts 32-1 and 32-2 denote two halves of a duckbill seal.

Having two such lines 26' provides more accurate positioning, since the positions of both lines may be followed when advancing the tape 18', and also even better liquid barrier properties, be it at the cost of a larger centre-to-centre distance. In addition, it is now easier and more reliable to seal unused reagent pads 19" from the environment. The reagent material is often very moisture sensitive, and therefore the unused part of the tape is often kept in a cassette. For example, in FIG. 1, the supply reel 17-1 is often in a closed housing, with the tape emerging from an exit opening. Such opening may be sealed, e.g. by means of a duckbill seal 32, or other type of seal. In this way, the unused reagent pads are well protected against moisture from the environment. It is furthermore noted that, although sealing is possible on the embodiments of FIGS. 2 and 3 as well, the embodiment of FIG. 4 has the advantage that positioning accuracy may be better due to the very sharp laser ablation lines 26, while the spacing between a set of two such lines 26' is very accurately controllable, and may be made to fit the dimensions of the seal 32 used. This prevents that liquid or moisture may seep through to the unused reagent pads between the seal 32-1, 32-2 via a laser ablation line. Note that a seal would not work right above such a laser ablation line 26, because of the absence of any material there, so that liquid could flow unhindered over the surface of the seal. This is topped by the narrow zone 31 of remaining material.

The above described embodiments only serve to help explain the invention without limiting this in any way. The scope of the invention is rather determined by the appended claims.

The invention claimed is:

1. A milking system, comprising a milking device with a milking control device and arranged for milking milk from a dairy animal, a milk line in fluid connection with the milking device, and a sampling and analysis device arranged to take a sample of the milk from the milk line and to analyse milk from the sample,
    wherein the milking control device is arranged to control the milking device on the basis of the analysis of the milk sample,
    wherein the sampling and analysis device comprises:
        a control unit for controlling the sampling and analysis device;
        a tape reel provided with a tape that is lengthwise provided with a series of consecutive reagent pads that are configured to provide a detectable response in the presence of at least one substance in the sample;
        a tape mover, arranged to move the tape under control of the control device;
        a dosing device arranged to supply a part of the sample onto a reagent pad on the tape under the control of the control unit;
        a camera operably connected to the control unit, and arranged to obtain an image of said reagent pad supplied with said droplet of the sample; and
        an analysis device to analyse the obtained images to provide to the milking control device an indication of a presence or concentration of said at least one substance,
    wherein the camera has a field of view that contains a plurality of reagent pads of the series of consecutive reagent pads,
    wherein the reagent pad comprises a bottom layer near the tape and stacked thereon a top layer,
    wherein at least the bottom layer comprises a reagent material configured to provide a detectable response in the presence of at least one substance in the sample, and
    wherein the top layer causes a first reaction before said detectable response can occur.

2. The milking system according to claim 1, wherein the tape mover is arranged to move the tape from a first position to a second position, wherein the sampling and analysis device is arranged to obtain images in at least the first position and the second position and to analyse said images obtained in at least the first position and the second position in order to provide said indication of a presence or concentration of said at least one sub stance.

3. The milking system according to claim 2, wherein the camera is arranged such as to have said field of view contain two, three or four reagent pads of the series of consecutive reagent pads.

4. The milking system according to claim 2, wherein the analysis device is arranged to obtain images of one of said reagent pads during at least a predetermined period of time, said predetermined period of time being at least as long as a multiple of an average length of time of milking one of said dairy animals.

5. The milking system according to claim 1, wherein the camera is arranged such as to have said field of view contain two, three or four reagent pads of the series of consecutive reagent pads.

6. The milking system according to claim 5, wherein the analysis device is arranged to obtain images of one of said reagent pads during at least a predetermined period of time, said predetermined period of time being at least as long as a multiple of an average length of time of milking one of said dairy animals.

7. The milking system according to claim 2, wherein the sampling and analysis device is arranged to simultaneously analyse the respectively milked milk of a plurality of consecutively milked dairy animals.

8. The milking system according to claim 5, wherein the sampling and analysis device is arranged to simultaneously analyse the respectively milked milk of a plurality of consecutively milked dairy animals.

9. The milking system according to claim 1, wherein the analysis device is arranged to obtain images of one of said reagent pads during at least a predetermined period of time, said predetermined period of time being at least as long as a multiple of an average length of time of milking one of said dairy animals.

10. The milking system according to claim 9, wherein the sampling and analysis device is arranged to simultaneously analyse the respectively milked milk of a plurality of consecutively milked dairy animals.

11. The milking system according to claim 1, wherein the sampling and analysis device is arranged to simultaneously analyse the respectively milked milk of a plurality of consecutively milked dairy animals.

* * * * *